(12) United States Patent
Lee et al.

(10) Patent No.: US 10,590,452 B2
(45) Date of Patent: Mar. 17, 2020

(54) DNA-MN HYBRID PARTICLES AND METHOD OF MANUFACTURING THE SAME

(71) Applicant: UNIVERSITY OF SEOUL INDUSTRY COOPERATION FOUNDATION, Seoul (KR)

(72) Inventors: Jong-Bum Lee, Seoul (KR); Jae-Sung Lee, Namyangju-si (KR)

(73) Assignee: UNIVERSITY OF SEOUL INDUSTRY COOPERATION FOUNDATION, Seoul (KR)

( * ) Notice: Subject to any disclaimer, the term of this patent is extended or adjusted under 35 U.S.C. 154(b) by 205 days.

(21) Appl. No.: 15/849,006

(22) Filed: Dec. 20, 2017

(65) Prior Publication Data

US 2019/0185895 A1    Jun. 20, 2019

(51) Int. Cl.
| | |
|---|---|
| *C12P 19/34* | (2006.01) |
| *C07H 23/00* | (2006.01) |
| *H01G 9/042* | (2006.01) |
| *C07H 1/00* | (2006.01) |

(52) U.S. Cl.
CPC .............. *C12P 19/34* (2013.01); *C07H 1/00* (2013.01); *C07H 23/00* (2013.01); *C12Y 207/07007* (2013.01); *H01G 9/042* (2013.01)

(58) Field of Classification Search
CPC ... C07H 23/00; C07H 21/04; C12Q 2531/125
See application file for complete search history.

(56) References Cited

U.S. PATENT DOCUMENTS

| | | | | |
|---|---|---|---|---|
| 2019/0002943 A1* | 1/2019 | Mazutis | ............ | B01L 3/502784 |
| 2019/0185924 A1* | 6/2019 | Adie | .................... | C12Q 1/6844 |

FOREIGN PATENT DOCUMENTS

| | | |
|---|---|---|
| KR | 1998-701695 A | 6/1998 |
| WO | 1996/023069 | 1/1996 |

OTHER PUBLICATIONS

Seung Woo Lee et al. Organic-inorganic hybrid nanoflowers:types, characteristics, and future prospects, Journal of Nanobiotechnology, Sep. 4, 2015, pp. 1-10.
Donna M. Joyce et al. Deoxyribonucleic acid-based hybrid thin films for potential application as high energy density capacitors,J. Appl. Phys. Mar. 20, 2014, pp. 114108-1-114108-5, vol. 115.

\* cited by examiner

*Primary Examiner* — David C Thomas
(74) *Attorney, Agent, or Firm* — Goldilocks Zone IP Law

(57) ABSTRACT

This invention relates to DNA-Mn hybrid particles and a method of manufacturing the same, the method including producing a circular DNA template for replication and forming particles in which DNA and Mn are bound to each other using Mn during the synthesis of a new strand of DNA from the circular DNA template for replication using a DNA polymerase, thus promoting the activity of the DNA polymerase using the coenzyme function of Mn and broadening the range of application fields of DNA as a biomaterial.

9 Claims, 12 Drawing Sheets

Specification includes a Sequence Listing.

[Fig. 1A]
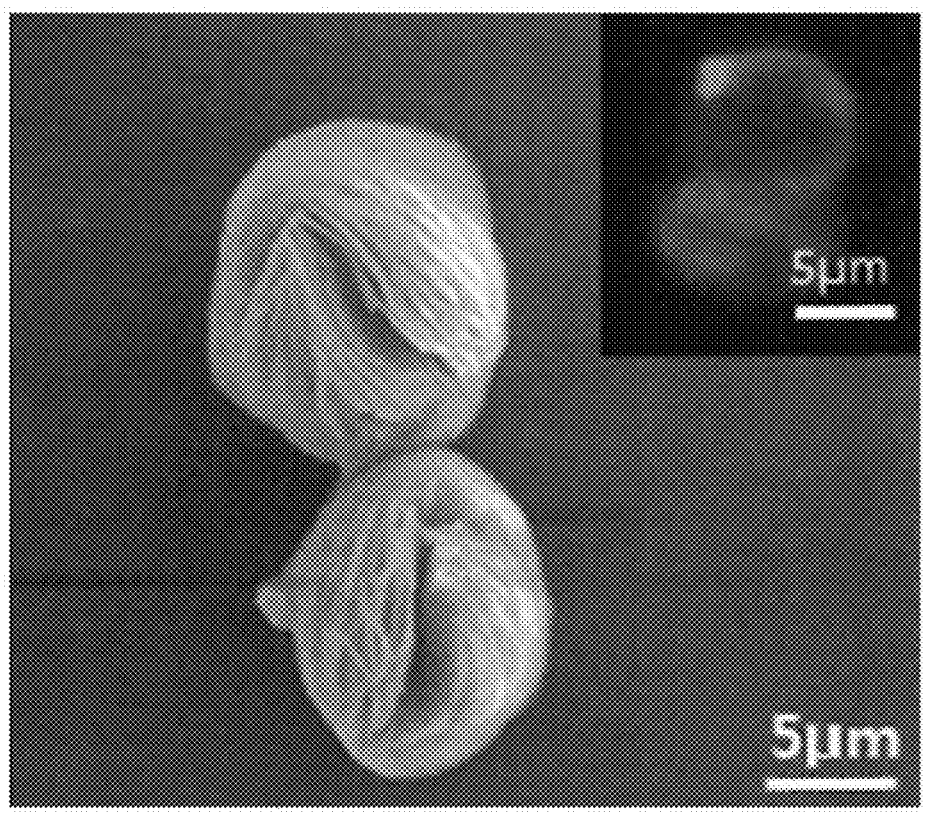

[Fig. 1B]
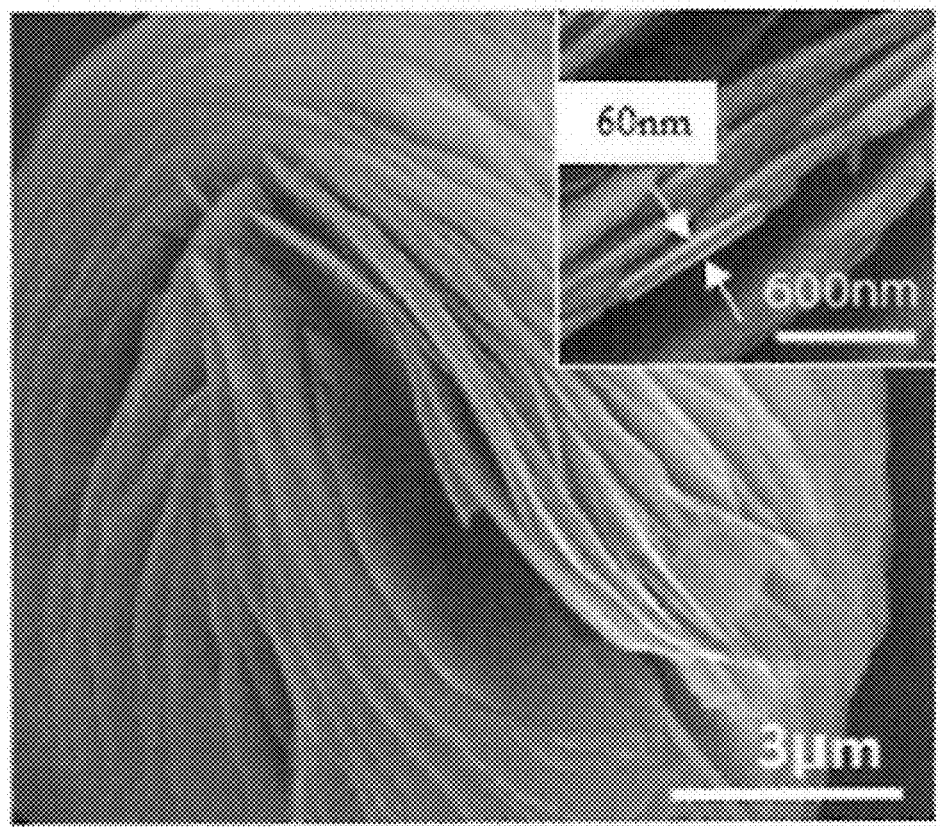

[Fig. 2]
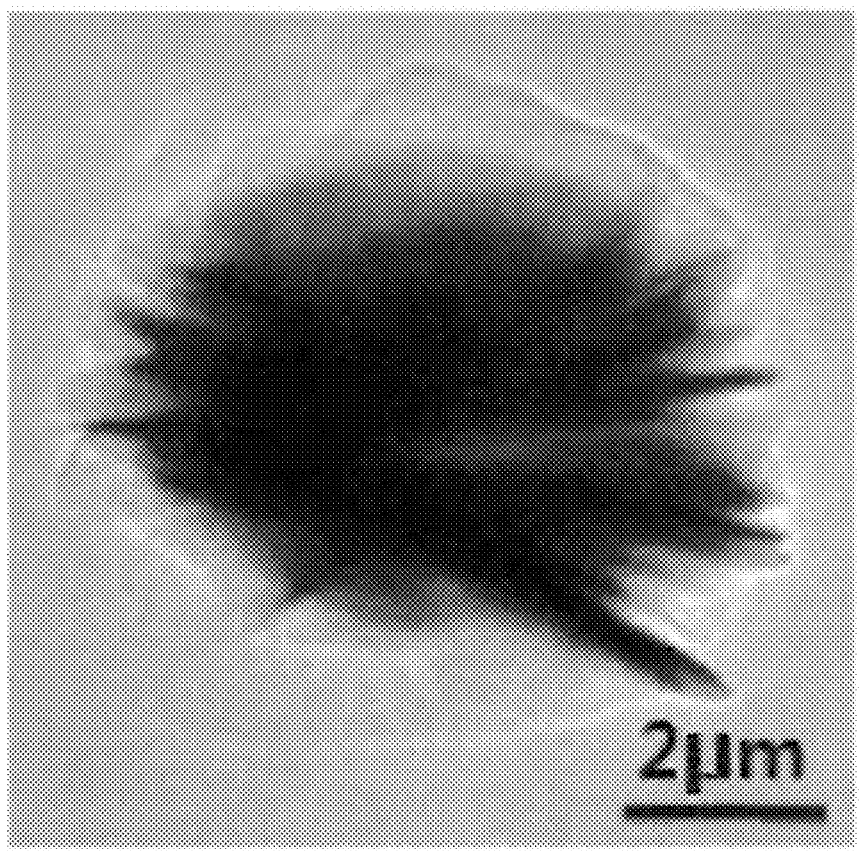

[Fig. 3]

[Fig. 4A]
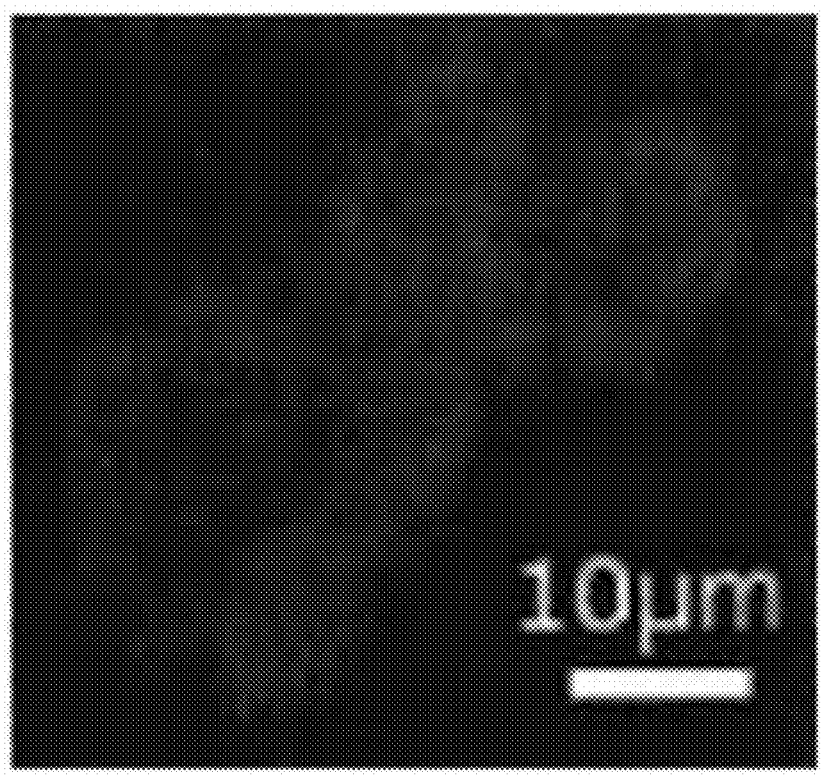

[Fig. 4B]
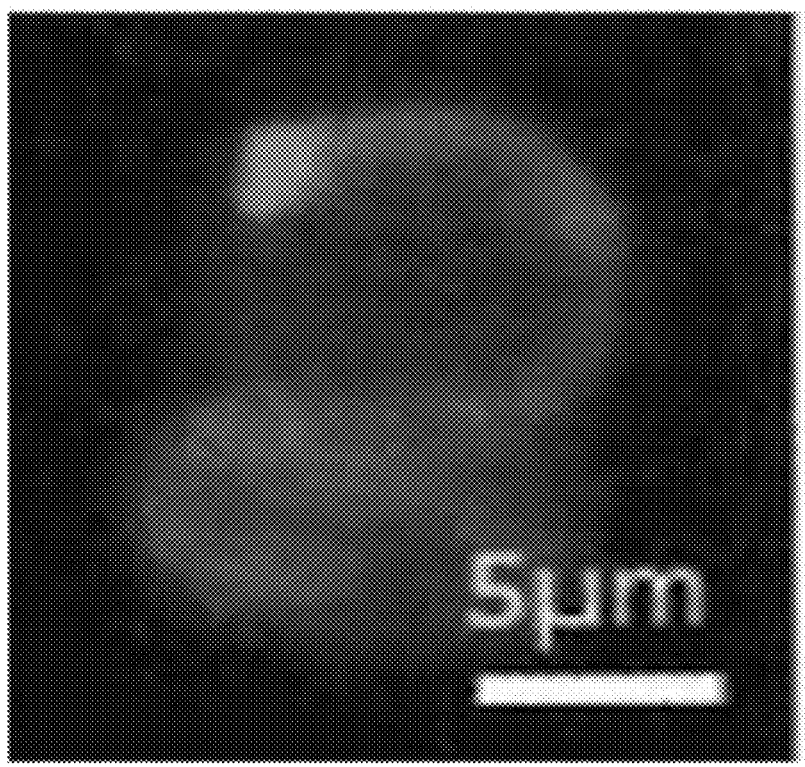

[Fig. 4C]
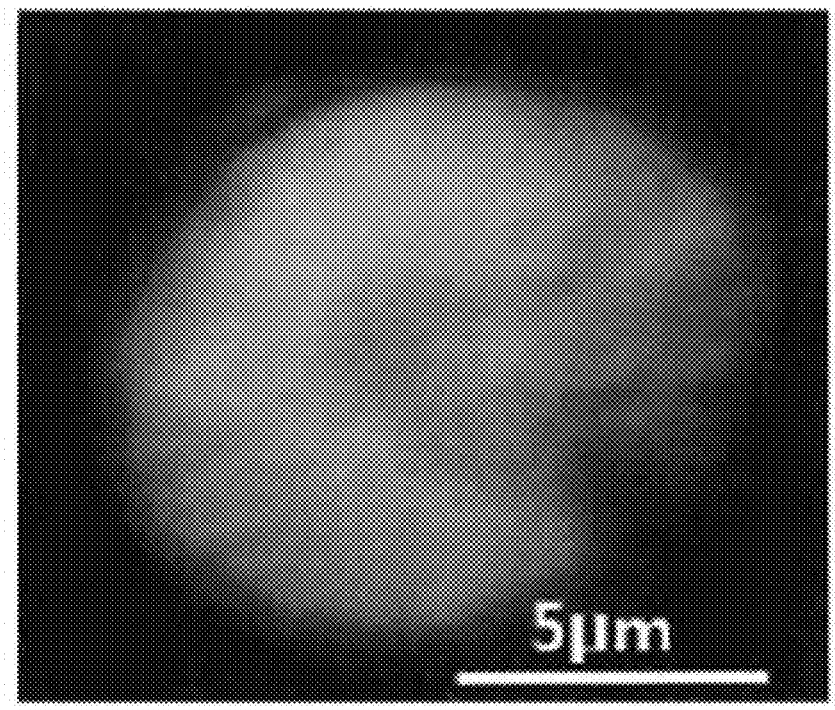

[Fig. 5]
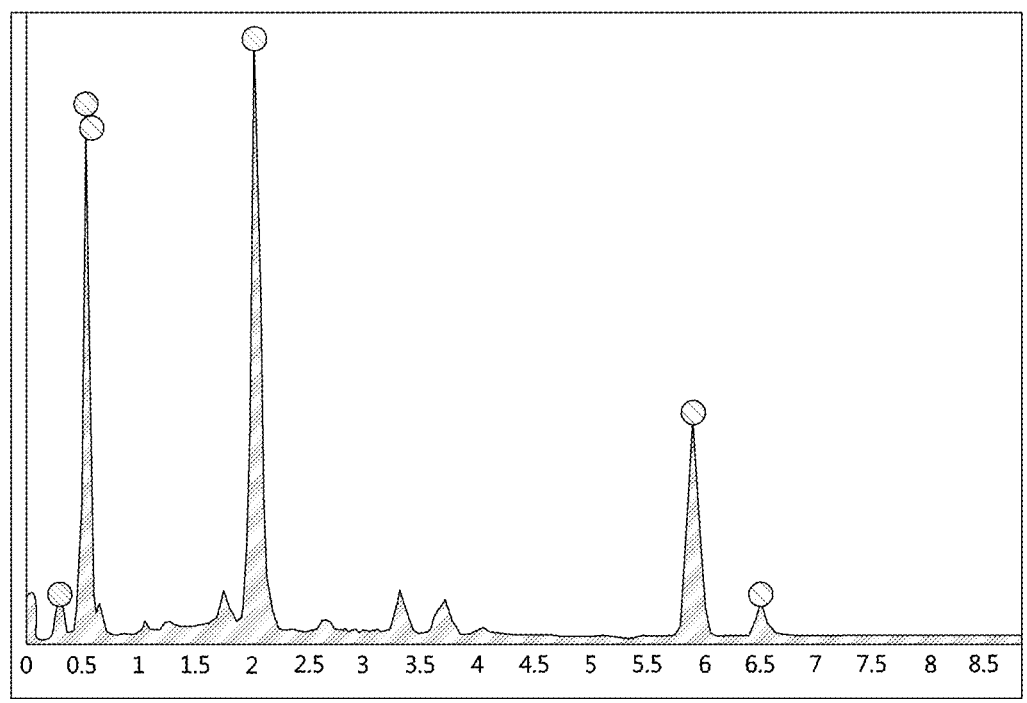

[Fig. 6A]
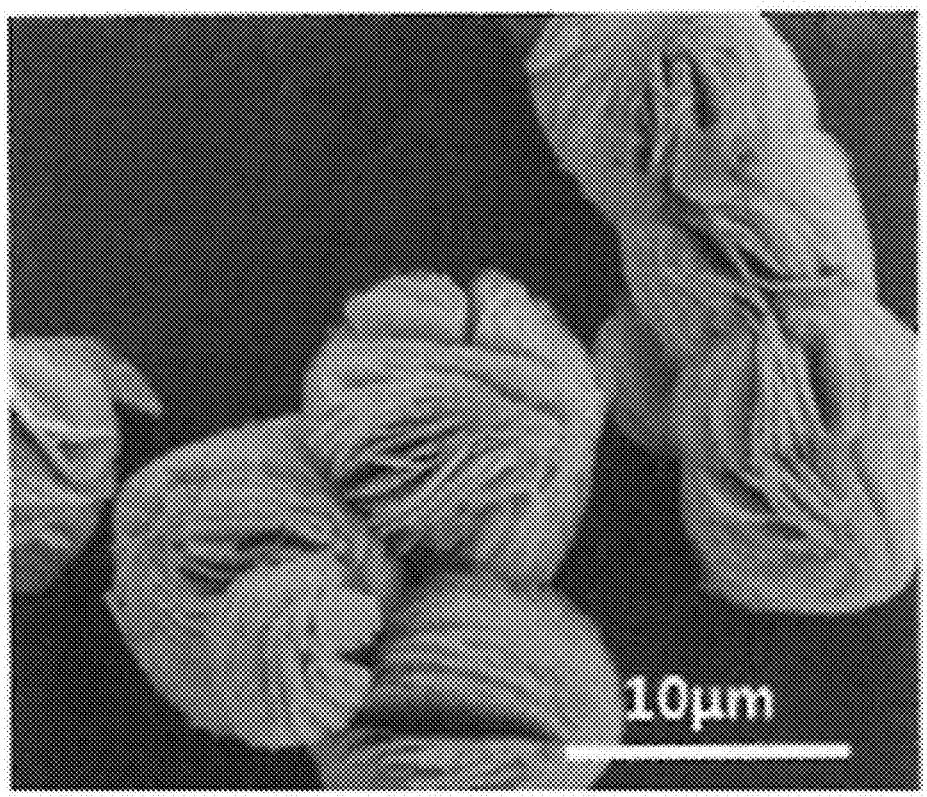

[Fig. 6B]
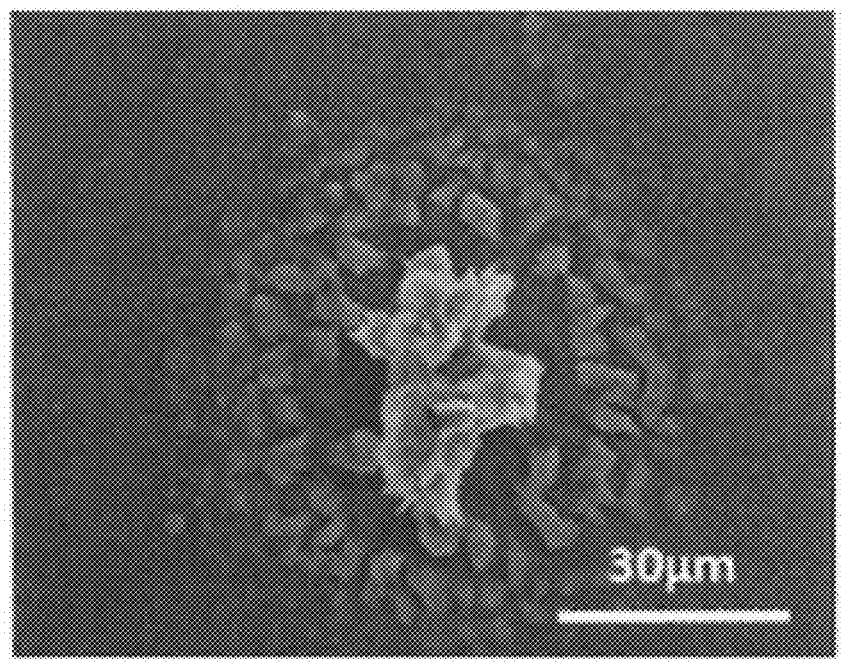

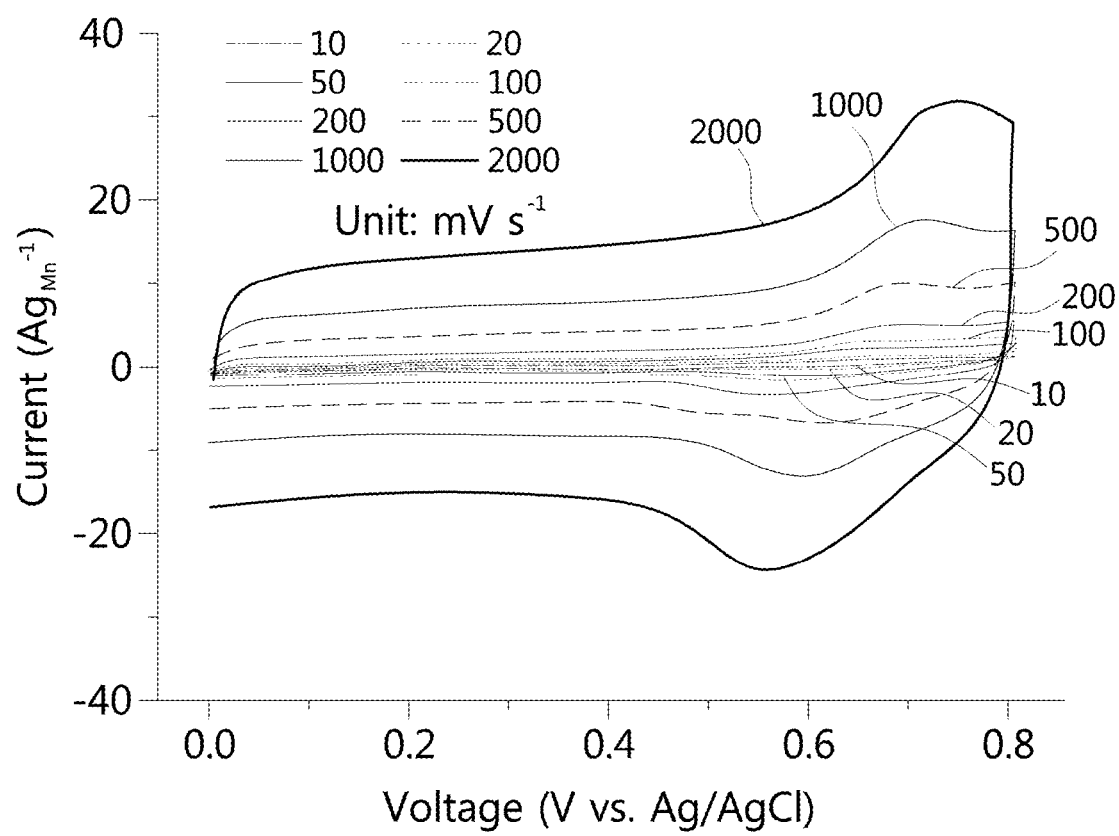
[Fig. 7A]

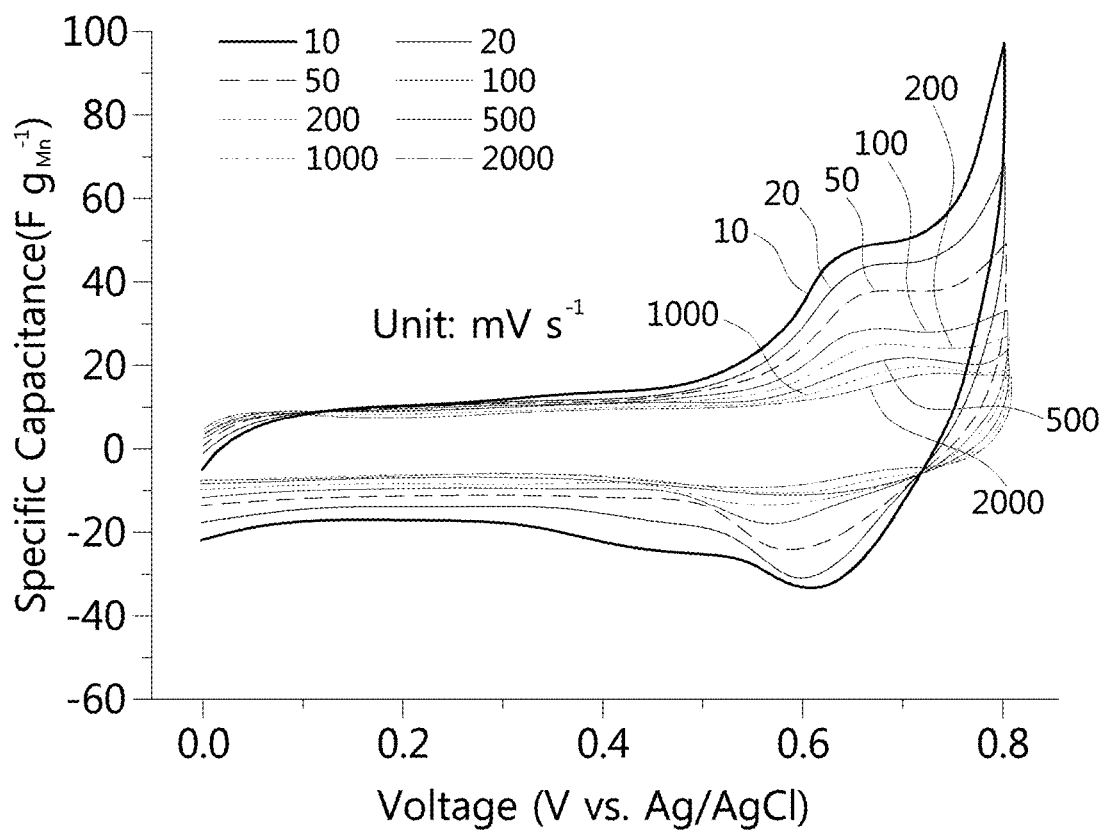
[Fig. 7B]

DNA-MN HYBRID PARTICLES AND METHOD OF MANUFACTURING THE SAME

STATEMENT REGARDING SPONSORED RESEARCH OR DEVELOPMENT

This invention was made with Korean Government support of Grant NO. NRF-2016M3A9C6917402 and NRF-2017M3D1A1039423, awarded by the Bio & Medical Technology Development Program of the National Research Foundation of Korea, funded by the Ministry of Science and ICT, Republic of Korea.

BACKGROUND OF THE INVENTION

1. Field of the Invention

The present invention relates to DNA-Mn hybrid particles and a method of manufacturing the same, and more particularly to DNA-Mn hybrid particles and a method of manufacturing the same, the method including producing a circular DNA template for replication and forming particles in which DNA and Mn are bound to each other using Mn during the synthesis of a new strand of DNA from the circular DNA template for replication using a DNA polymerase, thus promoting the activity of the DNA polymerase by virtue of the coenzyme function of Mn and broadening the range of application fields of DNA as a biomaterial.

2. Description of the Related Art

Nucleic acids, such as DNA, RNA and the like, are receiving great attention as a biomaterial necessary for biotechnology due to the characteristics thereof. Recently, disease remedies using nucleic acids are being developed, and have been reported in the following Patent Literature.

PATENT LITERATURE

Korean Patent Application Publication No. 10-1998-0701695 (Laid-open date: Jun. 25, 1998) "Recombinant DNA in which DNA encoding myosin heavy-chain SM1 isoform protein is inserted into vector DNA, microorganism into which electro-recombinant DNA is introduced, and therapeutic agent for arteriosclerosis including recombinant DNA"

However, conventional techniques using nucleic acids are mainly limited to biotechnology, and techniques for utilizing nucleic acids such as DNA in fields other than biotechnology have not been widely studied, and there is a problem in that the state of completion of the technology is low.

Accordingly, there is an increasing need to develop a technique that may effectively utilize particles, manufactured by binding a material capable of imparting different functions to nucleic acids such as DNA, in fields other than biotechnology.

SUMMARY OF THE INVENTION

Accordingly, the present invention has been made keeping in mind the above problems encountered in the related art, and the present invention is intended to provide DNA-Mn hybrid particles having the properties of both DNA and Mn and a method of manufacturing the same.

In addition, the present invention is intended to provide DNA-Mn hybrid particles and a method of manufacturing the same, in which the formation of particles may be promoted by increasing the activity of a DNA polymerase by means of Mn, which is a component of the particles to be manufactured during the manufacturing process.

In addition, the present invention is intended to provide DNA-Mn hybrid particles and a method of manufacturing the same, in which a biomaterial, DNA, may be utilized as a material for an energy storage device.

The present invention is accomplished through the following exemplary embodiments.

An embodiment of the present invention provides a method of manufacturing DNA-Mn hybrid particles, including forming particles comprising DNA and Mn bound to each other using Mn during the polymerization of DNA using a DNA polymerase.

Another embodiment of the present invention provides a method of manufacturing DNA-Mn hybrid particles, including producing a circular DNA template for replication, and forming particles comprising DNA and Mn bound to each other using Mn during the synthesis of a new strand of DNA from the circular DNA template for replication using a DNA polymerase, wherein the forming the particles is performed in a manner such that the circular DNA template for replication, the DNA polymerase and a Mn compound are added together and reacted at a predetermined temperature for a predetermined period of time.

In the method of manufacturing DNA-Mn hybrid particles according to the present invention, the particles may have a spherical shape.

In the method of manufacturing DNA-Mn hybrid particles according to the present invention, each of the particles may have a multilayer structure.

In the method of manufacturing DNA-Mn hybrid particles according to the present invention, Mn may promote the activity of the DNA polymerase.

In the method of manufacturing DNA-Mn hybrid particles according to the present invention, the particles may be used as a material for an energy storage device.

In the method of manufacturing DNA-Mn hybrid particles according to the present invention, the particles may be changed in size and shape by adjusting the amount of Mn that is used.

In the method of manufacturing DNA-Mn hybrid particles according to the present invention, the producing the circular DNA template for replication may include hybridizing a primer and ssDNA having base sequences enabling complementary binding to the primer at both terminals thereof and an arbitrary base sequence at the center thereof through complementary binding, and ligating a nick using a ligase.

A further embodiment of the present invention provides DNA-Mn hybrid particles, comprising DNA and Mn bound to each other.

The DNA-Mn hybrid particles according to the present invention may have a spherical shape, and each of the spherical particles may have a multilayer structure.

According to embodiments of the present invention, the following effects may be obtained.

The present invention can effectively exhibit the properties of both DNA and Mn.

Also, the present invention can effectively promote the formation of particles by increasing the activity of a DNA polymerase by means of Mn, which is a component of the particles to be manufactured during the manufacturing process.

Also, the present invention can effectively use a biomaterial DNA as a material for an energy storage device.

BRIEF DESCRIPTION OF THE DRAWINGS

FIGS. 1A and 1B are scanning electron microscope (SEM) images of particles according to an embodiment of the present invention;

FIG. 2 is a transmission electron microscope (TEM) image of particles according to an embodiment of the present invention;

FIG. 3 is a 3D SEM image of particles according to an embodiment of the present invention;

FIGS. 4A to 4C are fluorescence microscope images of particles according to an embodiment of the present invention;

FIG. 5 is a graph showing the results of energy-dispersive X-ray spectroscopy (EDX) analysis of particles according to an embodiment of the present invention;

FIGS. 6A and 6B are SEM images of the manufactured particles depending on changes in Mn concentration; and FIGS. 7A and 7B are graphs showing the results of cyclic voltammetry of particles according to an embodiment of the present invention.

DESCRIPTION OF SPECIFIC EMBODIMENTS

Hereinafter, a detailed description will be given of DNA-Mn hybrid particles and a method of manufacturing the same according to the present invention, with reference to the appended drawings. Unless otherwise defined, all terms used herein have the same meanings as those commonly understood by one of ordinary skill in the art to which the present invention belongs. If the meaning of a term used herein conflicts with the general meaning thereof, the definition used herein shall prevail. In the following description of the present invention, detailed descriptions of known constructions and functions incorporated herein will be omitted when they may make the gist of the present invention unclear. As used herein, when any part "includes" any element, it means that other elements are not precluded but may be further included, unless otherwise mentioned.

An embodiment of the present invention addresses a method of manufacturing DNA-Mn hybrid particles, including forming particles comprising DNA and Mn bound to each other using Mn during the polymerization of DNA using a DNA polymerase. Specifically, the method of manufacturing the DNA-Mn hybrid particles includes producing a circular DNA template for replication and forming particles comprising DNA and Mn bound to each other using Mn during the synthesis of a new strand of DNA from the circular DNA template for replication using a DNA polymerase.

The producing the circular DNA template for replication may include hybridizing a primer and ssDNA having base sequences enabling complementary binding to the primer at both terminals thereof and an arbitrary base sequence at the center thereof through complementary binding, and ligating a nick using a ligase. The DNA for replication, obtained after the ligation process, has a completely circular shape.

The forming the particles comprising DNA and Mn bound to each other using Mn during the synthesis of a new strand of DNA from the circular DNA template for replication using a DNA polymerase may be performed in a manner in which the circular DNA template for replication, the DNA polymerase and the Mn compound are added together and reacted at a predetermined temperature for a predetermined period of time, thus obtaining DNA-Mn hybrid particles in which DNA and Mn are bound to each other. Here, Mn is an element that is abundantly present in the earth and is essentially necessary in traces amount in the human body. Upon the forming the particles, Mn is hybridized with DNA synthesized during polymerization while increasing the activity of the DNA polymerase, thereby manufacturing DNA-Mn hybrid particles. The DNA-Mn hybrid particles have a spherical shape, and each of the particles has a multilayer structure. Also, the amount of Mn that is used during the forming the particles is adjusted, and thus the size and shape of the particles may be changed. The DNA-Mn hybrid particles may be used as a material for an energy storage device.

Another embodiment of the present invention addresses DNA-Mn hybrid particles obtained by the method of manufacturing DNA-Mn hybrid particles as above.

A better understanding of the present invention will be given through the following examples, which are set forth to illustrate but are not to be construed as limiting the scope of the present invention.

<Example 1> Production of Circular DNA Template for Replication

1) A single-stranded DNA(ssDNA) was designed to have base sequences enabling complementary binding to a primer at both terminals thereof and an arbitrary base sequence at the center thereof, as follows: [5'-ATAGTGAGTCGTATTA (SEQ ID NO: 1)-ACGTACCAACAAATGTGAATGCA-GACCAAAGAATTACTTGAATTCTTTGGTCTGCAT-TCACATTTTA GAGGCAT(SEQ ID NO: 2)-ATCCCT (SEQ ID NO: 3)-3']. The primer was designed to have the nucleotide sequence SEQ ID NO: 4[5'-TAATACGACT-CACTATAGGGAT-3'].

2) Thereafter, ssDNA and the primer were placed in nuclease-free water so as to have concentrations of 10 µM, after which ssDNA and the primer were bound to each other using a thermal cycler (total volume of 100 µL).

3) Thereafter, in order to ligate a nick, the solution obtained by the procedure 2 of Example 1 was added with a ligase buffer and a T4 ligase at respective ratios of 1/10 and 1/50 relative to the total volume, followed by ligation at room temperature for 8 hr or more, thus yielding a circular DNA template for replication.

<Example 2> Formation of DNA-Mn Hybrid Particles

1) In order to replicate a new strand of DNA from the circular DNA template for replication, the circular DNA template for replication (0.3 pmol) was mixed with a phi29 DNA polymerase (500 units), rNTP mix (200 nmol), 40 mM Tris-HCl, 50 mM KCl, 5 mM $(NH_4)_2SO_4$, and 4 mM DTT (total volume of 100 µL).

2) To bind the replicated DNA with Mn, 2 mM $MnCl_2$ was mixed together during the procedure 1) of Example 2.

3) After the procedures 1) and 2) of Example 2, reaction was carried out at 30° C. for 20 hr, thereby manufacturing DNA-Mn hybrid particles.

<Example 3> Evaluation of Size and Shape of DNA-Mn Hybrid Particles

1) The particles obtained in Example 2 were analyzed using an SEM at different magnifications. The results are shown in FIGS. 1A and 1B. Also, the particles of Example 2 were analyzed using a TEM and a 3D SEM. The results are shown in FIGS. 2 and 3.

2) As shown in the SEM images of FIGS. 1A and 1B, spherical particles having a diameter of 7 to 10 μm were observed, and each of the spherical particles was composed of a multilayer structure, each layer having a thickness of about 60 nm. As is apparent from the TEM image of FIG. 2, the particles had a shape consistent with the shape seen in the SEM images of FIGS. 1A and 1B. The 3D structure of the spherical particles shown in the 3D SEM image of FIG. 3 was observed.

<Example 4> Evaluation of Components of DNA-Mn Hybrid Particles

1) The particles of Example 2 were stained using DNA dyes such as DAPI, SYBR Green and SYTOX Orange, and then analyzed using a fluorescence microscope (Eclipse Ti(Nikon)). The results are shown in FIGS. 4A to 4C.

2) The particles of Example 2 were observed through EDX. The results are shown in FIG. 5 and Table 1 below. FIG. 5 is a graph showing the results of EDX spectrum analysis, and Table 1 shows the element amounts of particles of Example 2.

TABLE 1

|  | Element | | | | | |
| --- | --- | --- | --- | --- | --- | --- |
|  | C | N | O | P | Mn | Total |
| Amount (%) | 13.10 | 4.13 | 61.74 | 12.77 | 8.27 | 100 |

3) As shown in FIGS. 4A to 4C, the particles exhibited strong fluorescence light and thus the particles of Example 2 were composed of DNA. As is apparent from FIG. 5 and Table 1, the particles of Example 2 were composed of carbon (C), nitrogen (N), oxygen (O), phosphorus (P), and manganese (Mn). Accordingly, the particles of Example 2 were found to comprise DNA and Mn.

<Example 5> Evaluation of Shape of DNA-Mn Hybrid Particles Depending on Changes in Mn Concentration 1) DNA-Mn hybrid particles were manufactured in the same manner as in Example 2, with the exception that 0.4 mM $MnCl_2$ was used in lieu of 2.0 mM $MnCl_2$.

2) The particles of Example 2 and the particles of the above 1) of Example 5 were analyzed using SEM. The results are shown in FIGS. 6A and 6B.

3) As seen in FIGS. 6A and 6B, depending on changes in the Mn concentration during the manufacturing process, the array of layers constituting the particles was altered, and thus the overall shape was also changed. This is because Mn affects the activity of the DNA polymerase.

<Example 6> Usability of DNA-Mn Hybrid Particles as Material for Energy Storage Device 1) Whether the particles of Example 2 were usable as a material for an energy storage device was evaluated through cyclic voltammetry. The results are shown in FIGS. 7A and 7B. The cyclic voltammetry testing was performed using a 3-electrode cell. Here, the particles of Example 2 were mixed with carbon and thus used as a working electrode, and Ag/AgCl (3M NaCl) and platinum were used as a reference electrode and a counter electrode, respectively. The data of FIGS. 7A and 7B were obtained from a 1.0M $Na_2SO_4$ aqueous solution, FIG. 7A showing the cyclic voltammogram plot of the electrode comprising DNA-Mn hybrid particles depending on changes in potential (V ws. Ag/AgCl) and sweep rate ($mVS^{-1}$), and FIG. 7B showing the specific capacitance plot of the electrode comprising DNA-Mn hybrid particles depending on changes in potential (V ws. Ag/AgCl) and sweep rate ($mVS^{-1}$).

2) Based on the results of measurement of current and specific capacitance in the voltage range from 10 mV/s to 2000 mV/s, a clear oxidation-reduction peak was observed, and exhibited the highest level of 92 $F/g_{M_n}$ at 10 mV/s (FIG. 7B). Also, the peak position was slightly shifted under various current density conditions (FIG. 7A). This is capable of being performed in a capacitor, which is one of the available types of energy storage devices, from which the particles of Example 2 can be concluded to be usable as a material for an energy storage device.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of manufacturing DNA-Mn hybrid particles, comprising forming DNA-Mn hybrid particles comprising DNA and Mn bound to each other using Mn during polymerization of DNA using a DNA polymerase, wherein the DNA-Mn hybrid particles are used as a material for an energy storage device.

2. A method of manufacturing DNA-Mn hybrid particles, comprising:
   producing a circular DNA template for replication; and
   forming DNA-Mn hybrid particles comprising DNA and Mn bound to each other using Mn during synthesis of a new strand of DNA from the circular DNA template for replication using a DNA polymerase,
   wherein the forming the DNA-Mn hybrid particles is performed in a manner such that the circular DNA template for replication, the DNA polymerase and a Mn compound are added together and reacted at a predetermined temperature for a predetermined period of time, and
   wherein the DNA-Mn hybrid particles are used as a material for an energy storage device.

3. The method of claim 2, wherein the DNA-Mn hybrid particles have a spherical shape.

4. The method of claim 3, wherein each of the DNA-Mn hybrid particles has a multilayer structure.

5. The method of claim 2, wherein the Mn promotes activity of the DNA polymerase.

6. The method of claim 2, wherein the DNA-Mn hybrid particles are changed in size and shape by adjusting an amount of Mn that is used.

7. The method of claim 2, wherein the producing the circular DNA template for replication comprises:
   hybridizing a primer and ssDNA having base sequences enabling complementary binding to the primer at both terminals thereof and an arbitrary base sequence at a center thereof through complementary binding; and
   ligating a nick using a ligase.

8. DNA-Mn hybrid particles, comprising DNA and Mn bound to each other, wherein the DNA-Mn hybrid particles are used as a material for an energy storage device.

9. The DNA-Mn hybrid particles of claim 8, wherein the DNA-Mn hybrid particles have a spherical shape and each of the spherical particles has a multilayer structure.

* * * * *

SEQUENCE LISTING

<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: region of ssDNA for binding primer

<400> SEQUENCE: 1
atagtgagtc gtatta                                                    16

<210> SEQ ID NO 2
<211> LENGTH: 74
<212> TYPE: DNA
<213> ORGANISM: Artificial Sequence
<220> FEATURE:
<223> OTHER INFORMATION: arbitrary region of ssDNA

```
<400> SEQUENCE: 2
acgtaccaac aaatgtgaat gcagaccaaa gaattacttg aattctttgg tctgcattca    60
cattttagag gcat                                                     74

<210> SEQ ID NO 3
<211> LENGTH: 6
<212> TYPE: DNA
<213> ORGANISM: Artificial Sequence
<220> FEATURE:
<223> OTHER INFORMATION: region of ssDNA for binding primer

<400> SEQUENCE: 3 atccct                                                               6

<210> SEQ ID NO 4
<211> LENGTH: 22
<212> TYPE: DNA
<213> ORGANISM: Artificial Sequence
<220> FEATURE:
<223> OTHER INFORMATION: primer for circular DNA generation

<400> SEQUENCE: 4
taatacgact cactataggg at                                             22
```